(12) United States Patent
Boitard et al.

(10) Patent No.: US 11,525,115 B2
(45) Date of Patent: Dec. 13, 2022

(54) PROCESS FOR THE ISOLATION AND ANALYSIS OF MICROORGANISMS CONTAINED IN A SAMPLE

(71) Applicant: MilliDrop Instruments SAS, St Mande (FR)

(72) Inventors: Laurent Boitard, Argenteuil (FR); Elisa Brambilla, Paris (FR); Denis Cottinet, Montrouge (FR)

(73) Assignee: EUROFINS MILLIDROP, Nantes (FR)

(*) Notice: Subject to any disclaimer, the term of this patent is extended or adjusted under 35 U.S.C. 154(b) by 552 days.

(21) Appl. No.: 16/678,093

(22) Filed: Nov. 8, 2019

(65) Prior Publication Data

US 2020/0148994 A1    May 14, 2020

(30) Foreign Application Priority Data

Nov. 12, 2018  (FR) ..................... 18 60440

(51) Int. Cl.
| | |
|---|---|
| C12M 1/36 | (2006.01) |
| C12M 3/00 | (2006.01) |
| C12M 1/02 | (2006.01) |
| C12M 1/00 | (2006.01) |
| C12Q 1/02 | (2006.01) |

(52) U.S. Cl.
CPC ............ *C12M 41/48* (2013.01); *C12M 23/44* (2013.01); *C12M 27/00* (2013.01); *C12M 41/14* (2013.01); *C12Q 1/02* (2013.01)

(58) Field of Classification Search
None
See application file for complete search history.

(56) References Cited

U.S. PATENT DOCUMENTS 9,851,345 B1    12/2017    Arab et al.

OTHER PUBLICATIONS

James Q. Boedicker et al.: "Detecting bacteria and determining their susceptibility to antibiotics by stochastic confinement in nanoliter droplets using plug-based microfluidics", Lab on a Chip, vol. 8, No. 8, Jan. 1, 2008 pp. 1265-1272.

(Continued)

*Primary Examiner* — James M Anderson, II
(74) *Attorney, Agent, or Firm* — B. Aaron Schulman, Esq.; Stites & Harbison, PLLC

(57) ABSTRACT

A process is provided for isolating and analyzing microorganisms contained in a sample by collecting a determined volume in a sample, the determined volume representing all or part of this sample, likely to contain at least one microorganism. The collected volume is then split up into a plurality of compartments having a culture medium, the volume of each compartment being smaller than 10 µL, each compartment being isolated from the other compartments and having no interface with the ambient atmosphere. At least one microorganism is incubated in the compartments for determined durations, and compartments are detected that contain at least one microorganism. The incubation may be extended after detecting compartments so that at least one microorganism having a defined quantity can be detected, and then the content of the detected compartments can be recovered. Finally, at least one functional parameter relative to a microorganism in the compartments is determined.

16 Claims, 5 Drawing Sheets

(56) References Cited

OTHER PUBLICATIONS

Dong-Ku Kang et al: "Rapid detection single bacteria in unprocessed blood using Integrated Comprehensive Droplet Digital Detection", Nature Communications, vol. 5, Nov. 13, 2014.
Kaushik Aniruddha M et al: "Accelerating bacterial growth detection and antimicrobial susceptibility assessment in integrated picoliter droplet platform", Biosensors and Bioelectronics, Science LTD.UK, Amsterdam, NL, vol. 97, Jun. 27, 2017, pp. 260-266.
Zhang Pengfei et al: "Spatially encoded picoliter droplet groups for high-throughput combinatorial analysis", 2017 19$^{th}$ International Conference on Solid-State Sensors, Solid State Sensors, Actuators and Microsystems (Transducers), Jun. 18, 2017, pp. 1797-1800.
Muhammad Asim Faridi et al:"Elasto-inertial micro-fluidics for bacteria separation from whole blood for sepsis diagnostics", Journal of Nanobiotechnology, vol. 15, No. 1, Jan. 4, 2017.
Laurent Boitard et al: "Growing microbes in millifluidic droplets", Engineering in Life Sciences, vol. 15, No. 3, Mar. 10, 2015, pp. 318-326.
Larysa Baraban et al: "Millifluidic droplet analyser for microbiology", Lab on a Chip, vol. 11, No. 23, Jan. 1, 2011, p. 4057.
Preliminary Search Report for French Application No. 1860440, Aug. 13, 2019, European Patent Office, Rijswijk, NL.

PROCESS FOR THE ISOLATION AND ANALYSIS OF MICROORGANISMS CONTAINED IN A SAMPLE

FIELD OF THE INVENTION

The present invention relates to a process for the isolation and analysis of microorganisms contained in a sample.

BACKGROUND OF THE INVENTION

To study functional parameters of microorganisms, such as a sensitivity to antibiotics, a particular metabolism, the production of toxins or an enzymatic activity, it is known to collect a sample, for example a blood sample of 10 mL, and to dilute it in a 40 mL blood culture vial as shown in FIG. 1. The collection is for example done in the laboratory. When the sample comes from a patient in whom an infection by a pathogenic microorganism, typically a bacterium, is suspected, a first antibiotic treatment is generally indicated to the patient while waiting for confirmation or invalidation of the nature of the suspected pathogenic microorganism and his sensitivity to an antibiotic.

In this example, the diluted blood sample is placed in an incubator, typically at a temperature of 37° C. for a duration from 6 hours to 5 days until microorganism growth is detected. If growth is detected, the blood culture is said to be positive. The blood culture is detected as positive on average 24 hours after initiating incubation. Positive blood cultures are picked up to sow Petri dishes comprising an agar medium in order to isolate the microorganisms. The picking up of positive blood cultures depends on the presence and availability of competent technical staff, which may lead to additional time frames of up to 24 hours. The positive vials are processed more or less quickly depending on the availability of staff in the laboratory and depending on the opening hours of the laboratory.

After 24 hours of additional incubation at 37° C., the microorganism is isolated in the form of individualized colonies on an agar medium.

These colonies are used to identify the infectious agent as well as to conduct sensitivity tests to antibiotics, called "antibiograms".

The identification requires a length of time of between 1 hour for the mass spectrometry analysis and 24 hours for culture methods. The sensitivity tests require a length of time of between 6 and 24 hours in order to obtain results.

Depending on the results, an adjustment of the antibiotic treatment is proposed, 48 to 72 hours after receiving the sample. The waiting times for results can vary, since the operators are not always available to handle the samples between the different steps, in particular depending on the work schedules of the laboratory.

Such a process is therefore long and tedious to carry out, and contamination can occur during several steps due to the many manipulations by operators. This contamination can thus distort the results of the identification and antibiotic sensitivity tests.

SUMMARY OF THE INVENTION

One aim of the invention is to provide a process significantly reducing the microorganism isolation and analysis time, and limiting the occurrence of contamination.

To that end, the invention relates to a process for isolating and analyzing microorganisms contained in a sample comprising the following steps:

collecting a determined volume in a sample, the determined volume representing all or part of this sample, likely to contain at least one microorganism, splitting the collected volume into a plurality of compartments comprising a culture medium, the volume of each compartment being smaller than 10 µL, each compartment being isolated from the other compartments and having no interface with the ambient atmosphere, incubating at least one microorganism in the compartments during a determined duration, before or during the incubation, detecting compartments comprising at least one microorganism, extending the incubation after detecting compartments comprising at least one microorganism until detecting a defined quantity of microorganism, recovering the content of the detected compartments comprising at least one microorganism in receptacles for subsequent use, determining at least one functional parameter relative to a microorganism in the compartments comprising at least one microorganism, wherein the steps for splitting, incubation, detection and determining at least one functional parameter are integrated into an automated system for isolating and analyzing microorganisms.

DETAILED DESCRIPTION

The process for isolating and analyzing microorganisms according to the invention may comprise one or more of the following features, considered alone or according to any technically possible combination:

the content of the compartments, in which at least one microorganism has been detected, is recovered in receptacles while the other compartments are eliminated;

the sample is a blood sample;

each compartment is a drop;

the functional parameter relative to a microorganism is a sensitivity to an antibiotic;

the process further comprises, after the detection step, a step for recovering at least part of the compartments comprising at least one microorganism outside the system for automated isolation and analysis of microorganisms;

the process further comprises a step for measuring a parameter indicative of the growth of a microorganism in the compartments at different moments;

the duration of the step for incubating at least one microorganism in the compartments is greater than 1 hour;

the process further comprises a step for preparing compartments for the determination of at least one functional parameter;

after prolongation of the incubation, the compartments comprising at least one detected microorganism cumulatively contain at least $10^3$ microorganisms;

the duration of the prolongation of the incubation is at least equal to 30 minutes.

The invention also relates to an automated system for the isolation and analysis of microorganisms contained in a sample, the system comprising:

a device for splitting a determined volume of a sample likely to contain at least one microorganism into a plurality of compartments whose volume is smaller than 10 μL, each compartment being isolated from the other compartments and having no interface with the ambient atmosphere, a device for incubating at least one microorganism in the compartments during a determined duration, a device for detecting compartments comprising at least one microorganism, and a device for determining at least one functional parameter, capable of determining at least one functional parameter relative to a microorganism in the compartments comprising at least one microorganism, characterized by a central control unit capable of controlling the incubating device and the detection device in order to perform:

an incubation of the at least one microorganism in the compartments during a determined duration, a detection of the compartments comprising at least one microorganism before or during the incubation, and a prolongation of the incubation.

The system for automated isolation and analysis of microorganisms according to the invention may comprise one or more of the following features, considered alone or according to any technically possible combination:

the system contains, in the incubation device, in the detection device or in the device for determining at least one functional parameter, a plurality of compartments whose volume is smaller than 10 μL;

the device for determining at least one functional parameter, capable of determining at least one functional parameter relative to a microorganism in the compartments comprising at least one microorganism, is capable of carrying out a sensitivity test to at least one antibiotic in the compartments;

the system comprises:

a tube, a module for generating a train of sequenced drops in a carrier fluid, each compartment corresponding to a drop, the module for generating a train of drops comprising the splitting device, and a device for circulating the train of drops in the tube, capable of circulating the train of drops between the splitting device, the incubating device, the detection device and the device for determining at least one functional parameter;

the incubating device comprises at least one drop storage device capable of being temperature-regulated.

BRIEF DESCRIPTION OF THE DRAWINGS

The invention will be better understood upon reading the following description, provided solely as an example, and done in reference to the appended drawings, in which:

FIG. 2 illustrates an example automated system for isolating and analyzing microorganisms 1.

Figure 1:
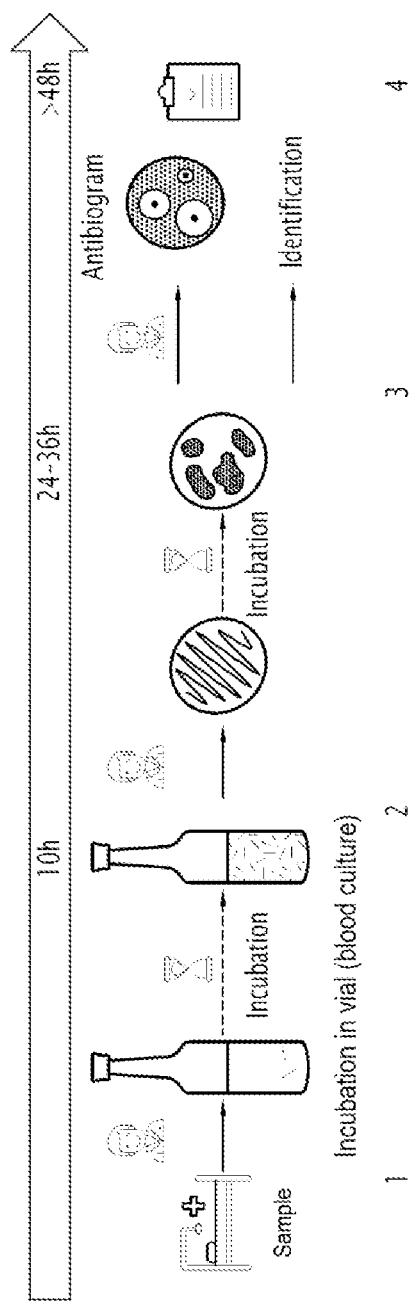
FIG. 1 is a schematic illustration of a process for isolating and analyzing microorganisms contained in a sample according to a known state of the art.

The automated system for isolating and analyzing microorganisms 1 is a system for isolating microorganisms 2 contained in a sample 4 capable of containing at least one microorganism and analyzing at least one functional parameter of the microorganisms 2. For example, the sample 4 contains a single species of microorganism 2. In a variant, the sample 4 contains several different species of microorganisms 2.

The microorganisms 2 are for example bacteria, yeasts, algae or filamentous fungi. The microorganisms 2 are for example prokaryotic or eukaryotic cells.

The microorganisms 2 are for example pathogenic microorganisms.

The sample 4 is for example a blood sample. Preferably, the sample 4 is a human blood sample.

In a variant, the sample 4 is a sample of urine, cerebrospinal fluid, bronchoalveolar fluid, skin sample or intestinal sample. According to this variant, the sample is a human or animal sample.

According to another variant, the sample 4 is a soil, food, beverage, bathwater, or industrial product sample.

Advantageously, the sample 4 comprises a culture medium 3.

The culture medium 3 comprises a liquid culture medium suitable for the survival and growth of the microorganisms 2 such as a buffered solution completed with culture nutrients, vitamins, electron donors and receivers. For example, the liquid culture medium 3 is Trypticase soy broth, Wilkins Chalgren broth, Yeast extract-Casein hydrolysate-Fatty Acids (YCFA), Cooked Meat Broth (CMB), Chopped Meat Carbohydrate Broth, Columbia broth, blood culture medium, Brain-heart infusion medium (BHIM), sheep stomach extract medium, Mueller-Hinton (MH) broth, Mueller-Hinton broth for fastidious bacteria (MH-F), or Wilkins Chalgren broth.

Advantageously, the culture medium 3 comprises microbial growth activators. For example, the culture medium 3 comprises factor X (hemin) and factor V (nicotinamide-adenine-dinucleotide, NAD), and vitamin B6.

Advantageously, the culture medium 3 comprises active, ion exchange resins, for the adsorption of molecules inhibiting the growth of certain microorganisms.

The automated system for isolating and analyzing microorganisms 1 according to the invention comprises a device for splitting 5 a determined volume of a sample likely to contain at least one microorganism 2 into a plurality of compartments 6 whose volume is smaller than 10 μL, each compartment 6 being isolated from the other compartments 6 and having no interface with the ambient atmosphere, an incubating device 7 for the microorganism(s) 2 in the compartments 6 during a determined duration, a detection device 8 of the compartments 6 comprising at least one microorganism 2, and a device for determining at least one functional parameter 9, capable of determining at least one functional parameter relative to a microorganism 2 in the compartments 6 comprising at least one microorganism 2.

Advantageously, the system 1 further comprises a device for preparing 11 compartments 6 for the determination of at least one functional parameter.

Advantageously, the system 1 comprises an enclosure incorporating the set of devices 5, 7, 8, 11, 9 of which it is composed.

Advantageously, at least one from among the incubating device 7, the detection device 8 and the device for determining at least one functional parameter 9 contains compartments 6.

Figure 2:
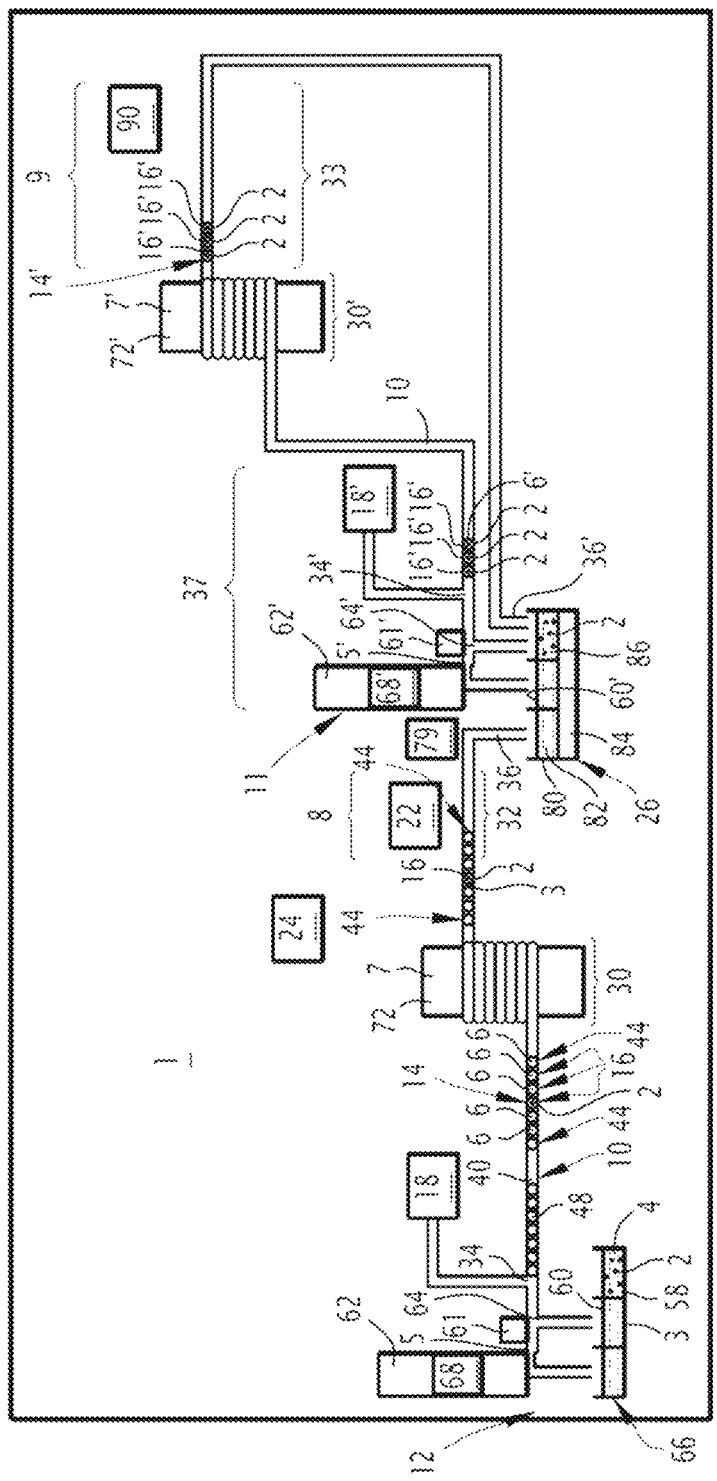
FIG. 2 is a schematic illustration of a system for isolating and analyzing microorganisms according to the invention.

In the automated system for isolating microorganisms 1 shown in FIG. 2, each compartment 6 is a drop 16, 16'.

The automated system for isolating and analyzing microorganisms 1 includes a tube 10, a module for generating 12 a train 14 of drops 16 suitable for circulating in the tube 10, and a device for circulating 18 the train 14 of drops 16 in the tube 10. The device for preparing 11 compartments 6 for the determination of at least one functional parameter is capable of generating a train 14' of drops 16'. Advantageously, the automated system for isolating and analyzing microorganisms 1 also includes a device for circulating 18' the train 14' of drops 16' in the tube 10. The tube 10 fluidly connects the splitting device 5, the incubating device 7 and the detection device 8 on the one hand, and the preparation device 11 of the compartments 6 and the device for determining at least one functional parameter 9 on the other hand.

The automated system for isolating and analyzing microorganisms 1 also comprises a measuring device 22 in the detection device 8, a central control unit 24 and a recovery device 26.

Hereinafter, the terms "upstream" and "downstream" and the terms "inlet" and "outlet" are used in reference to the normal circulation directions of the fluids in the system. The term "diameter" refers to the maximum span of the tube considered in a plane transverse, that is to say, perpendicular, to the central axis of the tube, for example, the diameter of a circle in the case where the transverse section of the tube is circular or the diagonal of a rectangle in the case where the transverse section of the tube is rectangular.

The tube 10 is a capillary tube or fluid tube on the millimetric scale, that is to say, having an inner diameter in the order of a tenth of a millimeter to a millimeter. Preferably, the tube 10 has an inner diameter of between 0.2 mm and 3 mm.

The tube 10 has an inner cross-section with a rounded or angle-free contour. For example, the tube 10 has a circular or elliptical cross-section, or polygonal, such as rectangular.

The tube 10 has at least an incubating area 30, a measuring area 32 and an area for determining a functional parameter 33. Furthermore, the tube 10 has at least one inlet end 34 and at least one outlet end 36.

Advantageously, the system 1 further has an area for preparing 37 compartments 6' for the determination of a functional parameter.

The module 12 for generating a train 14 of drops 16 is able to generate a train 14 of drops 16.

A train 14 of drops 16 is a sequenced series of drops 16 in a carrier fluid 40.

The carrier fluid 40 is advantageously an organic phase, in particular an oily phase. The carrier fluid 40 for example comprises hydrofluoroethers such as FC-40 or HFE-7500, forming a fluorinated oil. In a variant, the carrier fluid 40 comprises a silicone oil or an organic oil such as mineral oil.

The carrier fluid 40 is capable of separating two successive drops 16 of the train 14 of drops 16.

Each drop 16 comprises an inner fluid 48 that is not miscible with the carrier fluid 40. Immiscible means that the distribution coefficient between the two fluids is less than $10^{-3}$. The internal fluid 48 is advantageously an aqueous phase.

The train 14 of drops 16 advantageously comprises separators 44. A separator 44 is a volume of fluid that is not miscible with the carrier fluid 40 and not miscible with the inner fluid 48, or a gas bubble. The separator 44 promotes the spacing between two successive drops 16 of the train 14 of drops 16 to prevent the contact or fusion of the drops 16.

In an example that is not shown, the train 14 of drops 16 comprises a separator 44 between each drop 16.

Each drop 16 of the train 14 of drops 16 constitutes a compartment 6 isolated from the other compartments 6 and devoid of interface with the ambient atmosphere.

Each drop 16 is a culture drop formed from the sample 4.

The volume of each drop 16 of the train 14 of drops 16 is smaller than 10 µL. Preferably, the volume of each drop 16 of the train 14 of drops 16 is smaller than 5 µL. Preferably, the volume of the drops 16 of the train 14 of drops 16 is between 0.2 µL and 2 µL, still more preferably between 0.6 µL and 1.2 µL. Also preferably, the volume of the drops 16 of the train 14 of drops 16 is substantially equal to 1 µL.

In one example, the volume of the drops 16 of the train 14 of drops 16 is substantially the same from one drop 16 to the next.

The volume of the drops is studied so that each drop 16 can contain a sufficient quantity of microorganisms 2 necessary to implement a step for determining a functional parameter relative to a microorganism 2.

The drops 16 comprise the culture medium 3.

Preferably, at least one drop 16 comprises a microorganism 2.

In a variant, the drops 16 further comprise a growth indicator. For example, the indicator is a fluorescent reporter or a chromogenic reporter for metabolic activity. The fluorescent reporter is for example carboxyfluorescein diacetate (CFDA) or resazurin.

The growth indicator is for example a luminescent or bioluminescent metabolic activity reporter as indicator of the presence of ATP using a luciferase.

The drop 16 comprises signaling entities capable of indicating the presence in the drop 16 of an enzyme or other biomolecules, for example glycopeptides. For example, the signaling entities are fluorogenic substrates that indicate the presence of an enzyme, since they are modified by this enzyme. For example, the signaling entities are fluorogenic substrates that react with biomolecules of the cell membranes. For example, the fluorogenic substrates are linked to lectins or to another compound that comprises a zinc(II) dipicolylamine.

The drop 16 further comprises elements secreted by the microorganism 2 such as proteins or molecules. These secreted substances are capable of modifying the potential hydrogen (pH), the impedance, or the dissolved gas composition of the drop 16. For example, the drop 16 comprises signal entities capable of indicating the presence of secreted elements and allowing their quantification. For example, the signaling entities are fluorogenic substrates that indicate the presence of an enzyme. For example, the signaling entities are fluorogenic substrates that indicate the variation of the pH in solution.

The generating module 12 of the train 14 of drops 16 for example includes one or a plurality of sample reservoirs 58, one or a plurality of reservoirs 60 of fluids necessary for the formation of the train 14 of drops 16, a collection device 62 and an input circuit 64.

The generating module 12 further includes a complementary reservoir 61. The complementary reservoir 61 includes the carrier fluid 40.

For example, sample reservoirs 58, or reservoirs 60 of fluids necessary to form the train 14 of drops 16, are different compartments of a microtitration plate 66. In a variant, the reservoirs 58, 60 are test tubes such as Falcon® tubes or micro-tubes like those sold by Eppendorf®. In a variant, the reservoirs 58, 60 are blood collection tubes or blood culture vials.

A sample reservoir 58 comprises the sample 4. For example, other microorganism reservoirs 58 contain other samples 4.

For example, one reservoir 60 comprises the culture medium 3.

For example, other reservoirs 60 contain reagents to be placed in the drop 16 or carrier fluid 40 to prepare the drops 16. For example, other reservoirs 60 contain buffer solutions, signaling entities or additives to promote the growth of the microorganisms 2.

The collection device 62 is capable of withdrawing solutions in each of the reservoirs 58, 60 so as to form a train 14 of sequenced drops 16 in the carrier fluid 40.

For example, at least two sample reservoirs 58 each comprise a distinct sample 4. The train 14 of sequenced drops 16 contains a first series of drops 16 coming from the first sample reservoir 58 and a second series of drops 16 distinct from the first series of drops 16 coming from the second microorganism reservoir 58.

The collection device 62 is capable of preparing the train of drops in the inlet circuit 64.

For example, the collection device 62 includes a robotic pipetting arm. In a variant or additionally, the collection device 62 includes a suction head. The use of a robotic collection device 62 makes it possible to limit the space necessary for manipulations.

For example, the collection device 62 comprises a gas reservoir 68. The gas reservoir 68 is for example used to pressurize the various reservoirs 60, 61 in order to facilitate the collection. For example, the collection device 62 is capable of injecting a fluid into the inlet circuit 64 by pushing the fluid from the reservoir 60, 61 using gas into the inlet circuit 64.

In a variant or additionally, the collection device 62 includes a suction pump placed on a bypass on the tube 10. For example, the pump is placed at the outlet 36. According to another example, the pump is placed downstream from the detection device 8. The pump is capable of suctioning the different fluids and placing the reservoirs 60, 61 under a vacuum. For example, the pump is a compressor or a gerotor pump.

The collection device 62 advantageously comprises a robot capable of preparing the content of the reservoirs 60 in the enclosure of the system.

The inlet circuit 64 is connected to the inlet 34 of the tube 10. The inlet circuit 64 includes the splitting device 5 capable of generating drops 16 from the collected sample 4 and a carrier fluid 40.

For example, the splitting device 5 consists of a recess or a step facilitating the splitting of the fluids and the generation of the drops 16. In a variant, the splitting device 5 consists of a flow focusing junction, or a T junction.

The carrier fluid 40 is for example injected, at the inlet circuit 64, along the tube 10 by the injection device so as to form the drops 16 of the train 14 of drops 16 by co-flow.

The device for circulating 18 the train 14 of drops 16 is capable of moving the train 14 of drops 16 within the tube 10 from the inlet 34 to the outlet 36.

The circulating device 18 for example comprises a blower unit and/or a suction unit.

The circulating device 18 is advantageously capable of circulating the train 14 of drops 16 from the incubating area 30 to the measuring area 32, then from the measuring area 32 to the incubating area 30. The drops 16 can thus be moved in both directions in the tube 10.

For example, the measuring area 32 is located downstream from the incubating area 30. The circulating device 18 is able to cause the drops 16 to go from the incubating area 30 to the measuring area 32 in order to detect the drops 16 comprising at least one microorganism 2 and to measure the parameter indicative of the content of the drops 16. The circulating device 18 is also capable of causing the drops 16 to go from the measuring area 32 to the incubating area 30 in order to continue the incubation of the drop 16.

The circulating device 18 is capable of generating a flow rate of the train 14 of drops 16 and carrier fluid 40 in the tube of between 0.1 mL/h and 100 mL/h.

The incubating device 7 is an incubating device of the train 14 of drops 16 in the tube 10.

The incubating device 7 is capable of inspecting the temperature of the incubation area 30 of the tube 10. For example, the incubating device 7 is capable of heating or cooling the incubation area 30 of the tube to a temperature of between 4° C. and 100° C., for example between 20° C. and 50° C., and in particular at 37° C. In one example, in order to isolate and analyze microorganisms associated with human pathologies, the temperature is set to 37° C.

The incubating device 7 comprises at least one storage device for the drops 16 capable of being temperature-regulated. The device for storage of the drops 16 is for example a spool 72, the part of the tube 10 corresponding to the incubation area 30 being wound to form a spool 72. This winding makes it possible to reduce the necessary bulk in order to have a large incubation length.

Advantageously, the incubation device 7 comprises a plurality of spools 72. This makes it possible to perform several incubations in parallel, or to perform the incubation of a large number of drops. This is particularly advantageous in order to handle several samples 4 at the same time. An additional spool makes it possible to store the drops 16 during incubation.

Advantageously, when the number of spools 72 is greater than 2, several detection devices 8 and several generating modules 12 are used and each one is associated with at least one spool 72.

For example, the total length of tube 10 wound in the incubation area 30 is between 5 meters and 1000 meters. For example, each spool 72 contains a length of tube 10 of between 5 and 50 meters.

In a variant, the incubating device comprises a chamber delimited by thermally insulating walls, a heating and cooling element such as a Peltier module, a fan making it possible to circulate the content convection gas and a temperature probe.

The detection device 8 of the drops 16 comprising at least one microorganism 2 is for example arranged downstream from the incubation area 30.

The measuring device 22 is capable of measuring a parameter indicative of the content of the drops 16 in the tube 10 at the measuring area 32 at different moments.

For example, the parameter is representative of the growth of a microorganism in the drop 16 or of the survival of the cells. Such successive measurements make it possible both to detect the drops 16 comprising at least one microorganism 2, having a metabolic or division activity, and, for each drop 16, to produce kinetic growth curves within the drop 16 during the incubation.

For example, the measuring device 22 is capable of performing an optical density measurement, a light diffusion measurement and/or an analysis on an image of a drop.

In a variant or additionally, the measuring device 22 is capable of detecting or quantifying a protein.

For example, the measurement is an optical measurement, such as a fluorescence measurement, a light diffusion measurement, an image analysis, a Raman spectroscopy measurement or an infrared spectroscopy measurement. The fluorescence measurement can consist of measuring the autofluorescence of the microorganisms.

Advantageously, the measuring device 22 is capable of implementing a calibration in order to verify the quality of the measurements done.

The central processing unit 24 includes a memory and a microprocessor. The central processing unit 24 is capable of recording the data from the measuring device 22 for each drop 16.

The central processing unit 24 is capable of analyzing the measurements done for a drop 16 and inspecting the circulation of the drop 16 toward the preparation area 37 in order to determine a functional parameter, the continuation of the incubation, the recovery of the drop 16 or the discharge of the drop 16 depending on the result of the analysis.

Advantageously, the central processing unit 24 is capable of determining whether a microorganism 2 is detected in a drop 16 according to the measurements from the measuring device 22. The central processing unit 24 is capable of warning the user or the information system of the laboratory that a microorganism 2 has been detected in at least one drop 16, or of transmitting the number of drops 16 in which a microorganism 2 has been detected.

Advantageously, the central processing unit 24 is capable of deciding to extend the incubation of the drops 16 in the incubation area 30 in order to guarantee that the quantity of microorganisms 2 produced in the drops 16 is sufficient in light of the planned preparations and measurements in the system 1 or outside the system 1.

Also advantageously, the central processing unit 24 is capable of adjusting the prolongation of the incubation as a function of quantitative parameters calculated from measurements done on the drop 16 by the measuring device 22. Examples of quantitative parameters will be described hereinafter.

The central processing unit 24 is capable of determining whether the microorganism 2 present in the drop 16 belongs to a group of microorganisms according to quantitative parameters calculated from measurements done on the drop 16. For example, the quantitative parameters can make it possible to determine whether the microorganism 2 is Gram positive or Gram negative, or whether it involves a bacterium or a fungus. For example, the central processing unit 24 is capable of using the quantitative parameters to define ad hoc groups, that is to say, to perform a data partitioning, and to deduce a probability evaluation therefrom that the microorganisms 2 detected in the drops 16 belong to a plurality of species. The central processing unit 24 is able to notify the user or the information system of the laboratory of this probability of detection of a variety of microorganisms 2, which corresponds to a sample commonly designated as polymicrobial.

Advantageously, the system 1 comprises, downstream from the measuring device 22, a device 79 for adding at least one reagent. The device 79 for example comprises a plurality of reservoirs each capable of containing a reagent. The device 79 is capable of introducing the reagent into a drop 16 in which at least one microorganism 2 has been detected.

The reagent for example comprises matrix for MALDI mass spectrometry, enzymes, deoxyribonucleic acid (DNA) or ribonucleic acid (RNA).

The recovery device 26 for example comprises at least one recovery container 80 comprising several receptacles 82, and a movement device 84 for moving the recovery container 80 relative to the outlet 36 of the tube 10 such that each drop 16 to be recovered is transferred to a receptacle 82. The drops 16 to be discharged are for example transferred to a dedicated different receptacle 82 or another recovery container 80. For example, the drops 16 to be recovered are each transferred to a different receptacle 82. In another example, the central processing unit 24 is capable of determining, for each drop 16 to be recovered, whether it belongs to a group according to the quantitative parameters calculated from measurements done on the drop 16, and the drops belonging to a same group are all transferred into a single receptacle 82 but a different receptacle 82 for each group.

The recovered drops 16 are for example used for a characterization outside the system 1. The characterization is for example an identification of the microorganisms present or a Gram+/Gram− characterization. For example, the microorganisms 2 are characterized by MALDI-TOF mass spectrometry, or by the use of API galleries.

Advantageously, the recovery device 26 comprises a support suitable for the MALDI-TOF technique for the identification of microbial species.

Such a support is capable of being transferred automatically by a conveyor into a mass spectrometer suitable for performing the characterization.

The preparation device 11 of the compartments 6 for the determination of at least one functional parameter is capable of preparing new compartments 6' comprising microorganisms 2 coming from recovered drops 16 and for which one wishes to determine a functional parameter after having prepared several compartments 6'.

The preparation device 11 of the compartments 6' is capable of generating a train 14' of drops 16' and advantageously comprises the same elements as the generating module 12 of the train 14 of drops 16.

The preparation device 11 of the compartments 6' for example includes one or a plurality of microorganism reservoirs 86, one or a plurality of reservoirs 60' of fluids necessary for the formation of the train 14' of drops 16', a device for transferring microorganisms 2 coming from the drops 16 in the receptacles 82 toward the microorganism reservoirs 86, a collection device 62' and an input circuit 64'. The preparation device 11 of the compartments 6' further includes a complementary reservoir 61'. The complementary reservoir 61' includes carrier fluid 40.

The preparation device 11 of the compartments 6' further includes a plurality of antibiotic reservoirs and an inoculating device capable of inoculating an antibiotic coming from a reservoir in the drops 16'. For example, certain antibiotic reservoirs do not comprise antibiotics.

For example, the collection device 62' comprises a gas reservoir 68'.

The inlet circuit 64' is connected to the inlet 34' of the tube 10. The inlet circuit 64' includes a splitting device 5' capable of generating drops 16 from microorganisms 2 coming from recovered drops 16 and carrier fluid 40.

For example, the splitting device 5' consists of a recess or a step facilitating the splitting of the fluids and the generation of the drops 16'. In a variant, the splitting device 5' consists of a flow focusing junction, or a T junction.

The carrier fluid 40 is for example injected, at the inlet circuit 64', along the tube 10 by the injection device so as to form the drops 16' of the train 14' of drops 16' by co-flow.

A device for circulating 18' the train 14' of drops 16' is capable of moving the train 14' of drops 16' within the tube 10 from the inlet 34' to the outlet 36'.

Advantageously, the new compartments 6' are prepared with chemical substances useful for the determination of at least one functional parameter (antibiotics, fluorescent probes, etc.). Preferably, the preparation device 11 of the compartments 6' is capable of preparing different concentrations and/or different natures of chemical substance.

Advantageously, the new compartments 6' all comprise microorganisms 2 and are new drops 16' suitable for being circulated toward the area for determining a functional parameter 33.

Advantageously, the quantity of microorganisms 2 in the new drops 16' is the same for all of the drops. The quantity of microorganisms 2 is adjusted to a value of between 10 cells and 1000 cells per drop. Such values make it possible to guarantee the validity of the results and their interpretation in line with the recommendations for the reference organisms.

For example, the central processing unit 24 is capable of determining the dilution steps that are necessary according to the quantitative parameters calculated from measurements done on the recovered drops 16 before their transfer.

For example, the microorganisms 2 coming from the recovered drops 16 and the receptacles 82 and used to prepare new compartments 6 are resuspended in one or a plurality of reservoirs of microorganisms 86 in a culture medium and diluted to achieve a controlled cell density. For example, this cell density is monitored owing to an optical density measurement. Advantageously, the central processing unit 24 is capable of recording this measurement. Advantageously, the central processing unit 24 is capable of determining the dilution steps that are necessary according to the optical density measurement and the quantitative parameters calculated from measurements done on the recovered drops 16 before their transfer.

Preferably, the inoculating device is capable of inoculating different antibiotic concentrations and/or antibiotics of different natures in each drop 16'.

The antibiotic concentrations in the reservoirs comprising an antibiotic are for example between 1 µg/L and 500 mg/L.

For example, the antibiotic is amoxicillin, cefoxitin, gentamicin, vancomycin and/or piperacillin-tazobactam.

Advantageously, the tube 10 has a second incubating area 30' arranged downstream from the preparation area 37 of the compartments 6 and upstream from the area for determining a functional parameter 33.

Advantageously, the second incubating area 30' includes an incubating device 7' identical to the incubating device 7. For example, the incubating device 7' includes a spool 72'.

The circulating device 18' is advantageously capable of circulating the train 14' of drops 16' from the preparation area 37 of the compartments 6' for determining a functional parameter to the second incubating area 30'.

The circulating device 18' is advantageously capable of circulating the train 14' of drops 16' from the incubating area 30' to the area for determining a functional parameter 33.

For example, the area for determining a functional parameter 33 is located downstream from the second incubating area 30'.

The device for determining at least one functional parameter 9 is capable of determining at least one functional parameter relative to a microorganism in the compartments comprising at least one microorganism.

For example, the functional parameter is relative to a sensitivity of a microorganism 2 to an antibiotic.

The device for determining at least one functional parameter 9 for example comprises a measuring device 90 substantially identical to the measuring device 22.

Preferably, the measuring device 90 is identical to the measuring device 22. The functional parameter is representative of the growth of a microorganism in the drop 16' in the presence of antibiotic or of the survival of the cells in the presence of antibiotic.

The central processing unit 24 is capable of analyzing the measurements done for a drop 16'. For example, if the functional parameter is relative to the sensitivity of a microorganism 2 to an antibiotic, the central processing unit 24 is capable of determining a minimum inhibiting concentration from measurements on the drops 16' in the device for determining at least one functional parameter 9. Advantageously, the central processing unit 24 is also capable of optionally using the quantitative parameters calculated from measurements done in the detection device 8 for the drops 16 recovered and used to determine at least one functional parameter 9, and optionally also using the optical density measurement done to inspect the density of cells before preparing the new drops 16', in order to determine the minimum inhibiting concentration.

For example, the system 1 comprises a display device, capable of displaying the results of the analysis of the measurements. Also for example, the system 1 comprises a device for printing a medium containing the results of the analysis of the measurements.

In a variant that is not shown, the preparation device 11 of the compartments 6' comprises a cassette placed at an output of the tube and provided with a plurality of reservoirs each comprising culture medium, an antibiotic and/or a chemical substance useful for determining at least one functional parameter. The cassette is provided with an inoculating device capable of inoculating part of the drops recovered in the reservoirs. Each reservoir is a compartment isolated from the other compartments and the ambient atmosphere. For example, the cassette comprises between 30 and 1000 reservoirs. Each reservoir is configured to comprise, at the end of preparation, an antibiotic concentration of between 1 µg/L and 500 mg/L. For example, some reservoirs do not contain antibiotic.

For example, the reservoirs are covered by a closing device capable of being opened during the inoculation of drops in the reservoirs and capable of being closed in the absence of inoculation of drops in the reservoir. The closing device for example comprises solenoid valves. The closing device is for example controlled by the central processing unit.

Preferably, at least two reservoirs comprise a different antibiotic. Also preferably, at least two reservoirs comprise different concentrations of a same antibiotic.

According to this variant, the device for determining at least one functional parameter comprises a device for moving the cassette relative to the outlet of the tube such that the drops to be analyzed are used to inoculate the reservoirs or the compartments that comprise an antibiotic.

Advantageously, the dimensions of the system 1 are such that it can be arranged on a lab table. In one example, the system 1 measures 1452 mm long, 810 mm deep and 993 mm high. In another example, the system 1 measures 810 mm long, 760 mm deep and 635 mm high.

Advantageously, the system 1 comprises an integrated cleaning device capable of rinsing, cleaning and testing the cleanliness of the devices integrated into the system 1. According to one specific embodiment, the automated system for isolating and analyzing microorganisms comprises an atmosphere inspection device. This allows the culture of specific microorganisms, in particular anaerobic microorganisms, which die or have a slower growth kinetic when they are exposed to dioxygen at an atmospheric content, and can use fermentation.

The process for isolating and analyzing microorganisms according to the invention will now be described, in reference to FIG. 2.

The process comprises supplying an automated system 1 for isolating and analyzing microorganisms.

The sample reservoirs 58 are filled with the samples 4 capable of containing at least one microorganism 2 and the reservoirs 60 with the fluids necessary for the formation of the train 14 of drops 16.

For example, this preparation is manual; in a variant, it is done by a robot.

The process further comprises collecting a determined volume in a sample 4.

The collection device 62 collects solutions in each of the reservoirs 58, 60 so as to form a train 14 of sequenced drops 16 in the carrier fluid 40.

The volume collected in the sample 4 is typically between 35 mL and 45 mL, preferably equal to 40 mL.

The process further comprises splitting the collected volume into a plurality of compartments 6 comprising a culture medium 3, the volume of each compartment 6 being less than 10 µL, each compartment being isolated from the other compartments and devoid of an interface with the ambient atmosphere, incubating the at least one microorganism 2 in the compartments 6 during a determined length of time, before or during the incubation, detecting compartments 6 comprising at least one microorganism 2, prolonging the incubation after the detection and determining at least one functional parameter relative to a microorganism 2 in the compartments 6 comprising at least one microorganism 2.

The splitting, detection and determining steps of the process are integrated into the automated system 1 for isolating and analyzing microorganisms.

The automated system for isolating and analyzing microorganisms is for example the system 1 of FIG. 2. According to this example, the process comprises generating a sequenced train 14 of drops 16 in a carrier fluid 40, circulating the train 14 of drops 16 in the tube 10, incubating the train 14 of drops 16 in the tube 10, and measuring at least one parameter indicative of the content of the drops 16 in the tube 10 at different moments during the incubation.

The train 14 of drops 16 is generated by the generating module 12 of the train 14 of drops 16.

In one example, for a sample of human blood of 10 mL mixed with 40 mL of culture medium, between 1000 drops and 100,000 drops, preferably between 10,000 drops and 50,000 drops, still more preferably between 39,500 drops and 40,500 drops are generated in order to form one or several trains of drops.

For example, the train 14 of drops 16 is circulated at a flow rate of 10 mL/h.

The incubating area 30 of the tube is kept at a temperature of 37° C.

The incubation is done in the incubating area 30 of the tube 10.

The incubation is done by successive phases; a measurement is done at the end of each incubation phase.

Advantageously, each incubation phase has a duration greater than 1 hour.

For example, in total, the incubation lasts between 1 hour and 120 hours, preferably between 1 hour and 72 hours, preferably between 3 and 24 hours, still more preferably between 3 hours and 10 hours.

During the step for detecting compartments comprising at least one microorganism in division or having a metabolic activity, each drop 16 is placed in the measuring area 32. The measurement for example comprises measuring a fluorescence signal indicative of the growth of the microorganism 2 in the drop 16.

This operation is for example repeated during the step for measuring a parameter indicative of the growth of a microorganism 2 in the drop 16.

According to one particular embodiment, the drop 16 is placed in the measuring area 32 before the incubation step.

Advantageously, the process further comprises a step for analyzing the measurements done for the drop 16, circulating the drop 16 toward the preparation area 37 in order to determine a functional parameter, continuing the incubation, recovering the drop 16 or discharging the drop 16 depending on the result of the analysis. This step is carried out by the central processing unit 24.

For example, once the presence of a microorganism is detected in a drop 16, the drop 16 is circulated toward the preparation area 37 in order to determine a functional parameter, or the drop 16 is recovered.

Advantageously, the growth speed is determined by the central processing unit 24. After slowing of the growth of the microorganism, the drop 16 is circulated toward the preparation area 37 in order to determine a functional parameter, or the drop 16 is recovered.

For example, when it is detected in the drop 16 that a molecule is produced by a microorganism 2 or a population of microorganisms, the drop 16 is circulated toward the preparation area 37 in order to determine a functional parameter, or the drop 16 is recovered in the recovery container 80.

If the measurement corresponds to a selection criterion of the user, for example when it is measured whether the microorganism is still in the exponential growth phase, the drop 16 is returned to the incubating area 30 by the circulation device 18. For example, this involves the incubating area 30 arranged upstream from the identification device 8. According to another example, this involves a new incubating area arranged downstream from the identification device 8.

The criterion is, for example, a final biomass quantity or a growth speed. For example, when it is detected that the drop 16 does not comprise microorganisms, the drop 16 is discharged. Likewise, if the measurement does not correspond to the selection criteria of the user, the drop 16 is discharged. In a variant, at least one drop 16 not comprising microorganisms is recovered for characterization outside the system 1 or circulation toward the preparation area 37 in order to determine a functional parameter. Such a drop 16 serves as a negative control for the characterization and/or determination of a functional parameter.

Preferably, the criterion is a final biomass quantity sufficient to carry out the step for determining at least one functional parameter relative to a microorganism 2. The drop 16 is placed back in the incubating area 30 by the circulating device 18 until reaching the desired quantity of microorganisms 2.

For example, the incubation is prolonged until the drops 16 identified as containing at least one living microorganism 2 cumulatively contain at least $10^2$ cells, at least $10^3$ cells, at least $10^4$ cells, at least $10^5$ cells or at least $10^6$ cells.

For example, the functional parameter is a sensitivity to an antibiotic.

According to one embodiment, the criterion is a quantity of microorganisms greater than or equal to $5.10^5$ microorganism cells per drop, or accumulated over a number of drops of between 1 and 50. This quantity makes it possible to prepare between 30 and 1000 compartments with $5.10^5$ cells per milliliter to produce an antibiogram.

For example, in total, the incubation is prolonged during a length of time of between 30 minutes and 5 hours for microorganisms with rapid growth, and up to 12 hours for microorganisms with slow growth.

According to this example, the drop 16 is next circulated toward the preparation area 37 of the compartments 6' for the determination of a functional parameter.

For example, before being recovered, the positive drop 16 undergoes an addition of reagents. The device 79 for adding at least one reagent inoculates at least one reagent in the drop 16. The reagent is for example chosen from among the matrix for MALDI mass spectrometry, enzymes, DNA and RNA.

The drop 16 is recovered in the recovery device 26.

For example, the microorganisms 2 coming from the recovered drops 16 and used to prepare new compartments 6' are resuspended in one or a plurality of reservoirs of microorganisms 86 in a culture medium and diluted to achieve a cell density inspected by an optical density measurement.

The process advantageously further comprises generating a train 14' of sequenced drops 16' in the carrier fluid 40. The train 14' of drops 16' is generated by the preparation device 11 of the compartments 6'.

In one example, between 30 drops 16' and 1000 drops 16' are generated to form one or several trains of drops.

For the step for determining at least one functional parameter relative to a microorganism 2, the drops 16' are for example inoculated with an antibiotic.

The inoculation device inoculates each drop 16' or several drops 16' in compartments containing an antibiotic coming from a reservoir.

The antibiotic concentrations are for example between 1 µg/L and 500 mg/L.

Preferably, the inoculation device inoculates different concentrations of a same antibiotic in each drop 16', and/or a different antibiotic in each drop 16'. The inoculation device inoculates and prepares each drop 16' such that the volume of each inoculated drop 16' circulated toward the area for determining a functional parameter 33 is less than 10 µL, or less than 1 µL.

The inoculated drops 16' are circulated toward the incubating area 30'. The inoculating area 30' of the tube 10 is kept at a temperature of 37° C.

The incubation is done in the incubating area 30' of the tube 10.

The incubation is done by successive phases; a measurement is done at the end of each incubation phase.

Advantageously, each incubation phase lasts 30 minutes.

For example, in total, the incubation lasts between 1 hour and 24 hours, or between 3 hours and 10 hours.

The drops 16' are next circulated toward the area for determining a functional parameter 33.

The determination of the functional parameter for example comprises measuring a fluorescence signal indicative of the growth of a microorganism in the presence of antibiotic in the drops 16'.

Advantageously, the process further comprises a step for analyzing measurements done for the drop 16, 16', and generating reports for results of this analysis. This step is carried out by the central processing unit 24. The results are for example displayed or printed by the display device or the printing device of the system 1.

For example, before or after the transfer to the area for determining a functional parameter 33, and/or at the end of analysis, the drops 16, 16' are recovered in the recovery container 80. Each selected drop 16, 16' is recovered in a receptacle 82.

Advantageously, the process further comprises a step for recovering at least part of the compartments 6 comprising at least one microorganism 2 outside the system 1 for automated isolation and analysis of microorganisms.

For example, the drops 16, 16' selected by the central processing unit 24 are recovered in the recovery container 80. Each selected drop 16, 16' is recovered in a receptacle 82'. The selected drops 16, 16' are for example used outside the system 1 in order to characterize the microorganisms 2 that they contain. The characterization is for example an identification of the microorganisms present or a Gram+/Gram-characterization. For example, the microorganisms 2 are characterized by MALDI-TOF mass spectrometry, or by the use of API galleries. The drops 16, 16' thus recovered are concentrated and allow a user to perform the analyses of his choice outside the system 1.

Advantageously, the recovered drops are prepared automatically in the system 1 on the medium suitable for the MALDI-TOF technique for the identification of microbial species and the medium thus prepared is transferred automatically by a conveyor in a mass spectrometer suitable for performing the measurement.

In a variant, the functional parameter is a quantity of nitrogen and phosphate that are metabolized by the microorganism, a quantity of toxins produced, or an enzymatic activity.

In a variant, the drops 16, 16' selected by the central processing unit 24 are grouped, manipulated and optionally redistributed. This makes it possible to guarantee that the set of results obtained in the system 1 and outside the system 1 can be considered descriptive of one same sample 4 or at least of the same population of microorganisms 2 coming from the initial sample 4.

In a variant, the determination of the functional parameter is carried out in a cassette placed at an outlet of the tube and provided with a plurality of reservoirs each comprising an antibiotic and an inoculating device capable of inoculating the drops selected in the reservoirs. Each reservoir is a compartment isolated from the other compartments and the ambient atmosphere. For example, the cassette comprises between 30 and 1000 reservoirs. Each reservoir is configured to comprise, at the end of preparation, an antibiotic concentration of between 1 µg/L and 500 mg/L. For example, some reservoirs do not contain antibiotic.

Advantageously, each reservoir comprises a microorganism growth indicator.

The closing device is closed; it covers the reservoirs. This makes it possible to limit the evaporation or deterioration of the antibiotics that they contain.

During the inoculation of drops in the reservoirs, the central processing unit controls the opening of the closing device.

The device for moving the cassette relative to the outlet of the tube moves the cassette such that the drops to be analyzed are used to inoculate the reservoirs or the compartments that comprise an antibiotic.

When the inoculation is completed, the central processing unit controls the closing of the closing device. The cassette is incubated for a determined length of time, for example between 1 hour and 24 hours, or between 3 hours and 10 hours.

The determination of the functional parameter for example comprises measuring a fluorescence signal indicative of the growth of a microorganism in the presence of antibiotic in the reservoirs.

The invention thus makes it possible to reduce the isolation and analysis duration of microorganisms, and to limit the occurrence of contamination by integrating, into a same automated system, the steps of splitting, incubating, detecting and determining at least one functional parameter relative to a microorganism.

Figure 3:
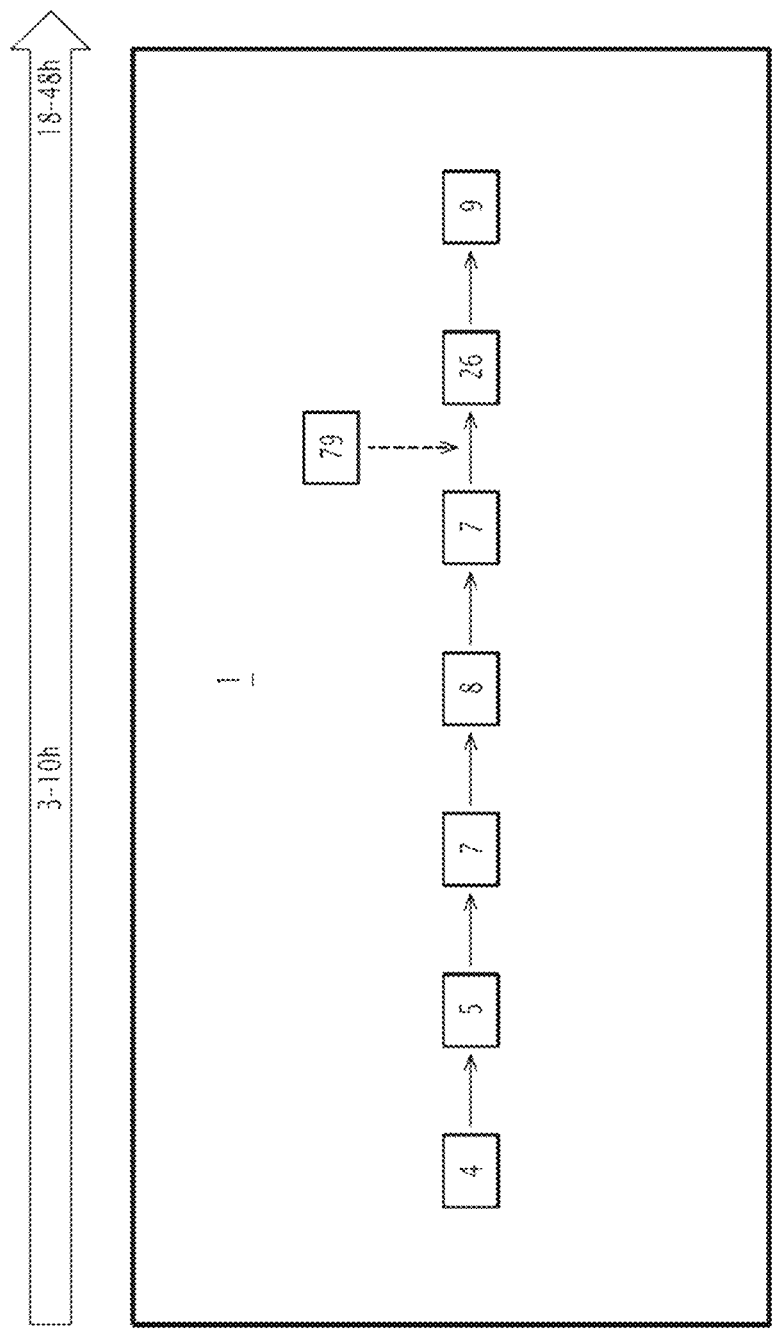
FIG. 3 is a view similar to FIG. 1 of a process according to the invention.

As illustrated in FIG. 3, the cumulative duration of the collection, splitting, incubation and detection steps is less than 48 hours, or less than 24 hours, or less than 12 hours.

The present invention will be illustrated in more detail by the example below.

EXAMPLE

This example demonstrates the detection and isolation of the bacteria by the culture after compartmentalization in drops and measurement of the Minimum Inhibiting Concentration on the isolated drops. In order to imitate patients' samples for the infection of the blood, the K12 MC4100 strain of Escherichia coli (E. coli) was diluted in 20 mL of Luria Broth medium to achieve less than 5 bacteria per milliliter. This very low initial cell density corresponds to the expected densities in positive blood samples. The tests were done with the Azur instrument sold by MilliDrop. The Azur instrument sold by MilliDrop makes it possible to:
- prepare up to 1000 drops, the volume of which is between 400 nL and 1 µL from 1 to 94 samples whose volume is between 30 µL and 20 mL,
- incubate the drops by measuring the fluorescence signal in each drop every 30 min,
- sort the drops, after incubation and measurement, so as to keep, among the 1000 drops, only those chosen according to the signal measured during the incubation.

Figure 4:
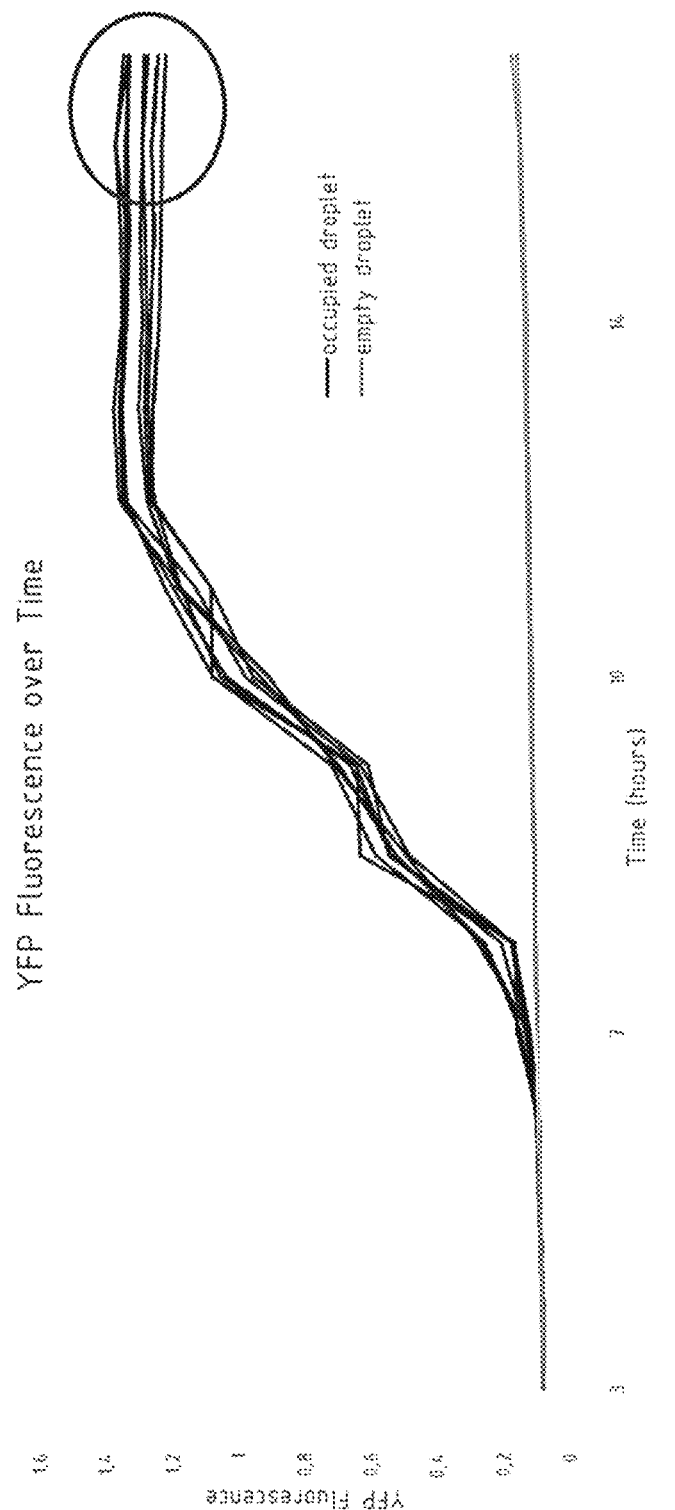
FIG. 4 is a curve showing the detection of droplets containing bacterial growth as a function of time using fluorescent marking.

This process has made it possible to detect the drops containing bacteria experiencing growth as of 8 hours after the preparation of the sample (FIG. 4). The drops containing bacteria experiencing growth are called positive drops. After such a detection of positive drops, the incubation is prolonged for 7 hours in order to accumulate enough biomass to inoculate the antibiotic sensitivity tests (AST). Next, the positive drops have been collected in a 96-well plate by using the drop sorting functionality of the Azur commercial instrument.

Figure 5:
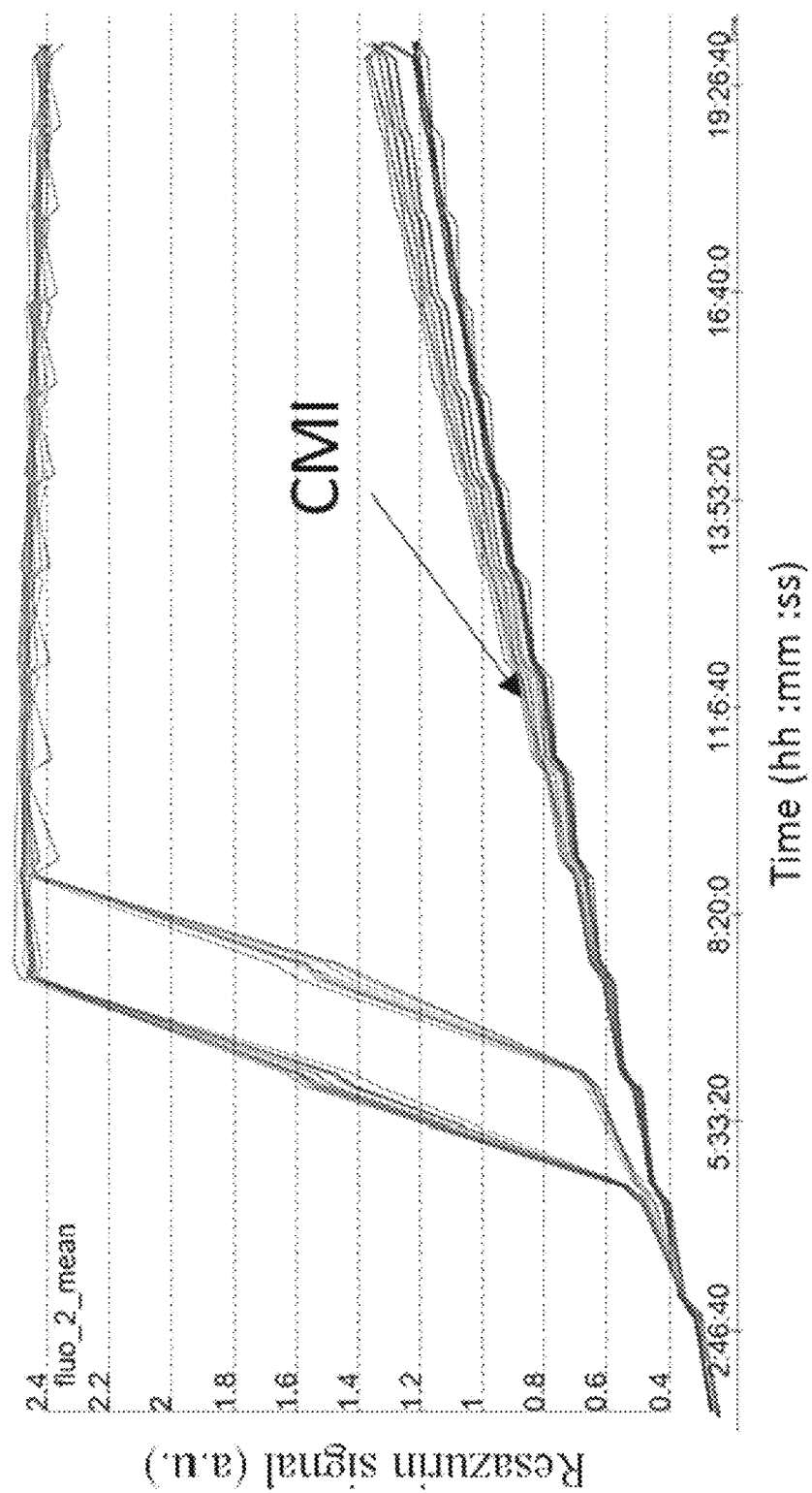
FIG. 5 is a curve showing the growth of strain K12 MC4100 of *Escherichia coli* in the presence of different concentrations of ampicillin.

A single collected positive drop was next used to inoculate all of the antibiotic concentrations prepared for the determination of the CMI. The inventors tested 10 concentrations for 3 different antibiotics. Each of these 30 conditions was reproduced in 30 drops, which represents 900 drops in all. The samples were prepared to achieve an inoculum of 100 cells per drop. Next, the incubation and the measurement of the drops last 8 hours in order to determine the CMIs (FIG. 5).

It has been demonstrated that the required incubation time between the reception of the sample and the AST was less than 24 hours for infectious strains whose growth speed is comparable to Escherichia coli. The entire process took 26 hours from preparation of the initial sample to obtaining the CMI results.

The invention claimed is:

1. A process for the isolation and analysis of microorganisms contained in a sample comprising:
   collecting a determined volume in a sample, the determined volume representing all or part of this sample, likely to contain at least one microorganism,
   splitting the collected volume into a plurality of compartments comprising a culture medium, the volume of each compartment being smaller than 10 µL, each compartment being isolated from the other compartments and having no interface with the ambient atmosphere,
   incubating at least one microorganism in the compartments during a determined duration,
   before or during the incubation, detecting compartments comprising at least one microorganism,
   extending the incubation after detecting compartments comprising at least one microorganism until detecting a defined quantity of microorganism,
   recovering the content of the detected compartments comprising at least one microorganism in receptacles for subsequent use,
   determining at least one functional parameter relative to a microorganism in the compartments comprising at least one microorganism,
   wherein the splitting, incubation, detection, and determining at least one functional parameter are integrated into an automated system for isolating and analyzing microorganisms.

2. The process for isolating and analyzing microorganisms according to claim 1, wherein the content of the compartments, in which at least one microorganism has been detected, is recovered in receptacles while the other compartments are eliminated.

3. The process for isolating and analyzing microorganisms according to claim 1, wherein the sample is a blood sample.

4. The process for isolating and analyzing microorganisms according to claim 1, wherein each compartment is a drop.

5. The process for isolating and analyzing microorganisms according to claim 1, wherein the functional parameter relative to a microorganism is a sensitivity to an antibiotic.

6. The process for isolating and analyzing microorganisms according to claim 1, wherein further comprising, after the detection, recovering at least part of the compartments comprising at least one microorganism outside the system for automated isolation and analysis of microorganisms.

7. The process for isolating and analyzing microorganisms according to claim 1, further comprising measuring a parameter indicative of the growth of a microorganism in the compartments at different moments.

8. The process for isolating and analyzing microorganisms according to claim 1, wherein the duration of the incubating at least one microorganism in the compartments is greater than 1 hour.

9. The process for isolating and analyzing microorganisms according to claim 1, further comprising preparing compartments for the determination of at least one functional parameter.

10. The process for isolating and analyzing microorganisms according to claim 1, wherein the incubation is prolonged until the drops identified as containing at least one living microorganism cumulatively contain at least $10^3$ cells.

11. The process for isolating and analyzing microorganisms according to claim 10, wherein the duration of the prolongation of the incubation is at least equal to 30 minutes.

12. An automated system for the isolation and analysis of microorganisms contained in a sample, the system comprising:

a splitting device for splitting a determined volume of a sample likely to contain at least one microorganism into a plurality of compartments whose volume is smaller than 10 μL, each compartment in said plurality of compartments being isolated from the other compartments and having no interface with the ambient atmosphere, incubation device for incubating at least one microorganism in the compartments during a determined duration, a detection device for detecting compartments comprising at least one microorganism, and a determination device for determining at least one functional parameter, said determination device capable of determining at least one functional parameter relative to a microorganism in the compartments comprising at least one microorganism, said system further comprising a central control unit capable of controlling the incubating device and the detection device in order to perform:

an incubation of the at least one microorganism in the compartments during a determined duration, a detection of the compartments comprising at least one microorganism before or during the incubation, and a prolongation of the incubation.

13. The automated system for isolating and analyzing microorganisms contained in a sample according to claim 12, the system containing, in the incubation device, in the detection device or in the determination device, a plurality of compartments whose volume is smaller than 10 μL.

14. The automated system for isolating and analyzing microorganisms contained in a sample according to claim 12, wherein the determination device is capable of carrying out a sensitivity test to at least one antibiotic in the compartments.

15. The automated system for isolating and analyzing microorganisms contained in a sample according to claim 12, comprising:

a tube, a generation module for generating a train of sequenced drops in a carrier fluid, each compartment corresponding to a drop, the module for generating a train of drops comprising the splitting device, and a circulation device for circulating the train of drops in the tube, said circulation device capable of circulating the train of drops between the splitting device, the incubating device, the detection device and the determination device.

16. The automated system for isolating and analyzing microorganisms contained in a sample according to claim 15, wherein the incubating device comprises at least one drop storage device capable of being temperature-regulated.

* * * * *